US012780749B2

(12) United States Patent
Gabbert

(10) Patent No.: US 12,780,749 B2
(45) Date of Patent: Nov. 3, 2026

(54) CONCRETE COUPON FOR RECOVERY OF BIOLOGICAL AGENTS

(71) Applicant: The Government of the United States of America, as represented by the Secretary of Homeland Security, Washington, DC (US)

(72) Inventor: Lindsay R. Gabbert, New London, CT (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 0 days.

(21) Appl. No.: 18/968,703

(22) Filed: Dec. 4, 2024

(65) Prior Publication Data

US 2025/0178973 A1 Jun. 5, 2025

Related U.S. Application Data

(60) Provisional application No. 63/606,169, filed on Dec. 5, 2023.

(51) Int. Cl.

| | |
|---|---|
| ***C04B 40/02*** | (2006.01) |
| ***A61L 2/06*** | (2006.01) |
| ***B28B 1/14*** | (2006.01) |
| ***B28B 7/24*** | (2006.01) |
| ***B28B 11/22*** | (2006.01) |
| ***C04B 40/00*** | (2006.01) |
| ***C04B 41/00*** | (2006.01) |
| ***C12Q 1/22*** | (2006.01) |

(52) U.S. Cl.

CPC ............ *C04B 40/0236* (2013.01); *A61L 2/06* (2013.01); *B28B 1/14* (2013.01); *B28B 7/24* (2013.01); *B28B 11/22* (2013.01); *C04B 40/0028* (2013.01); *C04B 40/0281* (2013.01); *C04B 41/0072* (2013.01); *C12Q 1/22* (2013.01)

(58) Field of Classification Search

CPC .............................. C04B 40/0236; C12Q 1/22

See application file for complete search history.

(56) References Cited

PUBLICATIONS

Gabbert, L. R., J. G. Neilan, and M. Rasmussen. "Recovery and chemical disinfection of foot-and-mouth disease and African swine fever viruses from porous concrete surfaces." Journal of Applied Microbiology 129.5 (2020): 1092-1101. (Year: 2020).*

Buhr, Tony L., et al. "Ultraviolet dosage and decontamination efficacy were widely variable across 14 UV devices after testing a dried enveloped ribonucleic acid virus surrogate for SARS-CoV-2." Frontiers in Bioengineering and Biotechnology 10 (2022): 875817. (Year: 2022).*

Meyer, K. M., et al. "Fumigation of a laboratory-scale HVAC system with hydrogen peroxide for decontamination following a biological contamination incident." Journal of applied microbiology 116.3 (2014): 533-541. (Year: 2014).*

Szostek, Adrianna. Evaluation of a Vehicle Undercarriage Decontamination System for Inactivating Newcastle Disease Virus. Diss. University of Delaware, 2019. (Year: 2019).*

* cited by examiner

*Primary Examiner* — Robert J Yamasaki

(74) *Attorney, Agent, or Firm* — Kelly G. Hyndman; Robert W. Busby

(57) ABSTRACT

In one example, a method of producing a concrete test coupon comprises: separating a coarse aggregate from a concrete mix to obtain a fine cementitious material; combining the fine cementitious material with water to obtain a wet concrete slurry; pouring the wet concrete slurry into a tray having one or more cavities to produce one or more concrete pieces; air drying the one or more concrete pieces in the tray; removing the one or more concrete pieces from the tray; carbonating the one or more concrete pieces to produce one or more carbonated concrete pieces; washing the one or more carbonated concrete pieces; and sterilizing the one or more carbonated concrete pieces.

20 Claims, 14 Drawing Sheets

| Test Number | BIT Solution Concentration | iHP Dose | Dwell Time | Aeration Time |
|---|---|---|---|---|
| 1 | 7.6% | 0.5mL/ft$^3$ | 15 Minutes | 2 Hours |
| 2 | 7.4% | 0.5mL/ft$^3$ | 15 Minutes | 2 Hours |
| 3 | 7.4% | 0.5mL/ft$^3$ | 1 Hour | 2 Hours |
| 4 | 7.4% | 0.5mL/ft$^3$ | Overnight (~16 Hours) | 2 Hours |

FIG. 5

Test #1 (7.6% Hydrogen Peroxide)
15 Minute Dwell Time

| | | Passage Number | | |
|---|---|---|---|---|
| | | 1 | 2 | 3 |
| ASFV | Steel | 0/36 | 0/36 | 0/36 |
| | Concrete | 0/36 | 0/36 | 0/36 |
| | | | | |
| FMDV | Steel | 0/36 | 0/36 | 0/36 |
| | Concrete | 1/36 | 6/36 | 8/36 |

FIG. 9

Test #2 (7.4% Hydrogen Peroxide)
15 Minute Dwell Time

| | | Passage Number 1 | 2 | 3 |
|---|---|---|---|---|
| ASFV | Steel | 0/36 | 0/36 | 0/36 |
| | Concrete | 0/36 | 0/36 | 0/36 |
| FMDV | Steel | 0/36 | 0/36 | 0/36 |
| | Concrete | 5/36 | 20/36 | 21/36 |

FIG. 10

Test #3 7.4% Hydrogen Peroxide
1 Hour Dwell Time

| | | Passage Number | | |
|---|---|---|---|---|
| | | 1 | 2 | 3 |
| **FMDV** | Concrete | 3/36 | 6/36 | 6/36 |

FIG. 11

Test #4 7.4% Hydrogen Peroxide
16 Hour Dwell Time

| | | Passage Number | | |
|---|---|---|---|---|
| | | 1 | 2 | 3 |
| FMDV | Concrete | 0/36 | 0/36 | 0/36 |

FIG. 12

| | | Positivity in Tests 1-4 | | | |
|---|---|---|---|---|---|
| Sample Location | Surface Type | 1 | 2 | 3 | 4 |
| 1 | Wall (Back) | + | - | + | - |
| 2 | Wall (Back) | - | - | - | - |
| 3 | Wall (Back) | - | - | - | - |
| 4 | Wall (Back) | - | - | - | - |
| 5 | Wall (Back) | - | - | - | - |
| 6 | Wall (Back) | - | + | - | - |
| 7 | Wall (side-right) | - | - | + | - |
| 8 | Wall (side-right) | - | - | - | - |
| 9 | Wall (side-right) | + | + | - | - |
| 10 | Wall (side-right) | - | - | - | - |
| 11 | Wall (Front) | - | + | - | - |
| 12 | Wall (Front) | + | + | - | - |
| 13 | Wall (Front) | - | + | - | - |
| 14 | Wall (Front) | - | + | + | - |
| 15 | Wall (Front) | - | + | + | - |
| 16 | Wall (Front) | - | + | - | - |
| 17 | Wall (side-left) | - | + | + | - |
| 18 | Wall (side-left) | + | + | - | - |
| 19 | Wall (side-left) | - | + | - | - |
| 20 | Wall (side-left) | - | + | - | - |
| 21 | Ceiling | - | + | - | - |
| 22 | Ceiling | - | + | - | - |
| 23 | Ceiling | - | + | - | - |
| 24 | Ceiling | + | + | - | - |
| 25 | Ceiling | - | + | - | - |
| 26 | Floor | - | - | - | - |
| 27 | Floor | + | - | - | - |
| 28 | Floor | - | + | - | - |
| 29 | Floor | - | + | - | - |
| 30 | Floor | - | + | - | - |
| 31 | Wall (under table) | - | + | - | - |
| 32 | Ceiling (side of light) | - | - | + | - |
| 33 | Floor (upside down) | + | - | - | - |
| 34 | Wall (in water trough) | - | - | - | - |
| 35 | Ceiling (top of railing) | - | - | - | - |
| 36 | Floor (under TOMI) | + | - | - | - |

FIG. 13

CONCRETE COUPON FOR RECOVERY OF BIOLOGICAL AGENTS

CROSS-REFERENCE TO RELATED APPLICATIONS

The application claims the benefit of priority from and is a non-provisional of U.S. Provisional Patent Application No. 63/606,169, filed on Dec. 5, 2023, entitled CONCRETE COUPON FOR PATHOGEN DETECTION, the disclosure of which is incorporated by reference in its entirety.

SUMMARY STATEMENT OF GOVERNMENT INTEREST

The present invention was made with support from the United States Department of Homeland Security (DHS) and by an employee of DHS in the performance of their official duties. The U.S. Government has certain rights in this invention.

FIELD

The discussion below relates generally to devices and methods for conducting microbial efficacy testing and, more specifically, to the recovery of biological agents from porous concrete test coupons.

BACKGROUND

Effective disinfection of environmental surfaces contaminated with pathogenic microorganisms is crucial to prevent, respond, and recover from infectious disease outbreaks. For high-consequence transboundary animal disease outbreaks due to an accidental or intentional release of agricultural pathogens, use of validated disinfection protocols ensures continuity of operations. During such outbreaks, disease transmission and geographical spread are often attributed to contamination of food, fomites, facilities, and transport vehicles with infectious agents. Effective cleaning and disinfection protocols result in destruction, inactivation, or elimination of the infectious agent.

Demonstration of validated disinfection procedures on porous materials such as wood, cloth, paper, and others have been historically difficult. Unsealed concrete is a porous material widely used in agricultural facilities, laboratories, and food processing plants where environmental contamination with microorganisms may occur. Validated decontamination and disinfection methods and protocols for unsealed concrete surfaces are notably lacking. Quantitative efficacy testing of chemical disinfectants applied to porous, unsealed concrete is often hindered by insufficient recovery of viral loads from concrete controls, resulting in critical knowledge gaps. Potential reasons for poor recovery of viable virus from unsealed concrete include irreversible physical adhesion of virus to the porous concrete substrate and viral inactivation after contacting the substrate.

Quantitative carrier tests are commonly used to assess disinfection methods for inactivation of microorganisms dried on various materials representing environmental surfaces. These standardized tests are typically conducted using nonporous coupons such as stainless steel or glass, and success is dependent upon sufficient recovery of microorganisms from untreated, positive control coupons. Insufficient recovery ($<4\text{-log}_{10}$) of viable virus from control coupons precludes demonstrating the minimum $4\text{-log}_{10}$ reduction in infectious titer required for virucidal efficacy determination and subsequent product registration with the U.S. Environmental Protection Agency.

Reliable experimental data for disinfection of microorganisms on unsealed concrete are limited because low recovery from concrete controls often prevents quantitative comparisons of treatments. For example, statistically significant differences have been reported in the recovery of vegetative bacteria from several porous coupon materials, with concrete and wood having the lowest recovery values. Additionally, attempts to recover viable, highly pathogenic avian influenza virus from concrete coupons by multiple extraction methods have failed.

Foot and mouth disease virus (FMDV) and African swine fever virus (ASFV) are high-consequence transboundary animal disease pathogens that cause severe economic consequences in endemic and epizootic countries. FMDV is a small, nonenveloped, positive-strand, RNA (+ssRNA) virus in the family Picornaviridae, and ASFV is a large, enveloped, double-stranded DNA (dsDNA) virus in the Asfarviridae family. Both pathogens are highly transmissible in domestic livestock populations and may persist in the environment for months under favorable conditions.

Disinfection of ASFV and FMDV on nonporous carriers, including sealed concrete, has been reported, but virus recovery from porous materials remains problematic. Insufficient recovery of FMDV was reported from untreated, porous concrete that resulted in inconclusive data for the chemical disinfectants tested. It was further reported that concrete coupons having pH ≥10 were virucidal to high-titer FMDV and ASFV and it was suggested that efficacy tests could only be conducted after sealing the concrete to render it nonporous.

Potential mechanisms responsible for low viral recovery from unsealed concrete include high pH, which may inactivate viruses, and the possibility that viral particles may become irreversibly bound to the concrete matrix. The pH of freshly prepared concrete is highly alkaline, measuring approximately pH 13. Both FMDV and ASFV are inactivated at PH levels ≥10, presumably due to loss of the structural integrity of the FMDV capsid and ASFV envelope.

Prolonged exposure to natural atmospheric and environmental conditions results in a gradual decrease in the pH of concrete over time. This process, termed carbonation, occurs due to the interaction of atmospheric carbon dioxide ($CO_2$) with the hydration products of cement, resulting in the formation of calcium carbonate ($CaCO_3$) and liberation of water: $Ca(OH)_2+CO_2CaCO_3+H_2O$. However, the chemical reaction is largely dependent on relative temperature and humidity, and thus may take many years to complete under natural conditions.

SUMMARY

The researchers have determined the influence of concrete pH on the recovery of infectious FMDV and ASFV. They compared virus recovery from untreated, high-pH concrete, and from concrete coupons in which the pH had been lowered through accelerated gaseous carbonation in a laboratory environment. Following demonstration of sufficient virus recovery from carbonated, pH-adjusted concrete, they conducted quantitative virucidal efficacy tests with a U.S. EPA-registered disinfectant using unsealed concrete coupons and dried inocula of FMDV and ASFV.

An aspect is directed to a method of producing a concrete test coupon. The method comprises: separating a coarse aggregate from a concrete mix to obtain a fine cementitious material; combining the fine cementitious material with water to obtain a wet concrete slurry; pouring the wet concrete slurry into a tray having one or more cavities to produce one or more concrete pieces; air drying the one or more concrete pieces in the tray; removing the one or more concrete pieces from the tray; carbonating the one or more concrete pieces to produce one or more carbonated concrete pieces; washing the one or more carbonated concrete pieces; and sterilizing the one or more carbonated concrete pieces.

In accordance with another aspect, a concrete test coupon comprises a sterilized, carbonated, dried concrete piece formed from a wet concrete slurry including a combination of water and a fine cementitious material which is obtained by separating a coarse aggregate from a concrete mix.

Other features and aspects of various examples and embodiments will become apparent to those of ordinary skill in the art from the following detailed description which discloses, in conjunction with the accompanying drawings, examples that explain features in accordance with embodiments. This summary is not intended to identify key or essential features, nor is it intended to limit the scope of the invention, which is defined solely by the claims.

BRIEF DESCRIPTION OF THE DRAWINGS

The attached drawings help explain the embodiments described below.

FIG. 5 is a Table of run conditions.

FIG. 9 is a Table of ASFV and FMDV results for Test #1 with 7.6% hydrogen peroxide.

FIG. 10 is a Table of ASFV and FMDV results for Test #2 with 7.4% hydrogen peroxide.

FIG. 11 is a Table of FMDV results for Test #3 with 7.4% hydrogen peroxide.

FIG. 12 is a Table of FMDV results for Test #4 with 7.4% hydrogen peroxide.

FIG. 13 is a Table of test results of location versus positivity.

DETAILED DESCRIPTION

A number of examples or embodiments of the present invention are described, and it should be appreciated that the present invention provides many applicable inventive concepts that can be embodied in a variety of ways. The embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure along with the knowledge of one of ordinary skill in the art.

Concrete is ubiquitously found in many manufacturing, laboratory, and clinical environments that are routinely decontaminated. However, most biological and chemical indicators used to monitor decontamination processes and efficacy are produced on non-porous surfaces that may not accurately represent the materials being decontaminated.

Embodiments of the present invention are directed to porous concrete testing coupons for use in microbial efficacy testing. In one example, a carbonated (low pH) concrete testing coupon can be spiked with the user's target organism and/or toxin and subjected to the decon (decontamination) process being tested to measure efficacy. The coupons can be used in testing the efficacy of liquid chemicals, gaseous fumigants/fogs/vapors, and physical decon methods such as heat and/or UV.

Concrete Coupon Production

Concrete was prepared in-house, based on mixing ratios indicated on the product label, after separating the coarse aggregate from an 80-pound bag of Sakrete High-Strength Concrete Mix and combining 438 g of the fine cementitious material with 100 mL of tap water (i.e., 438 g of the sifted concrete mix, absent of aggregate, was combined with 100 mL of tap water and mixed to create a wet slurry). Wet concrete slurry was poured into easy-release silicone ice cube trays to standardize size, shape, and volume (one hundred and sixty 1-$cm^3$ cubes/tray). Each cube volume is about 1 $cm^3$ (e.g., ±10% or ±5% or ±1%).

Figure 1:
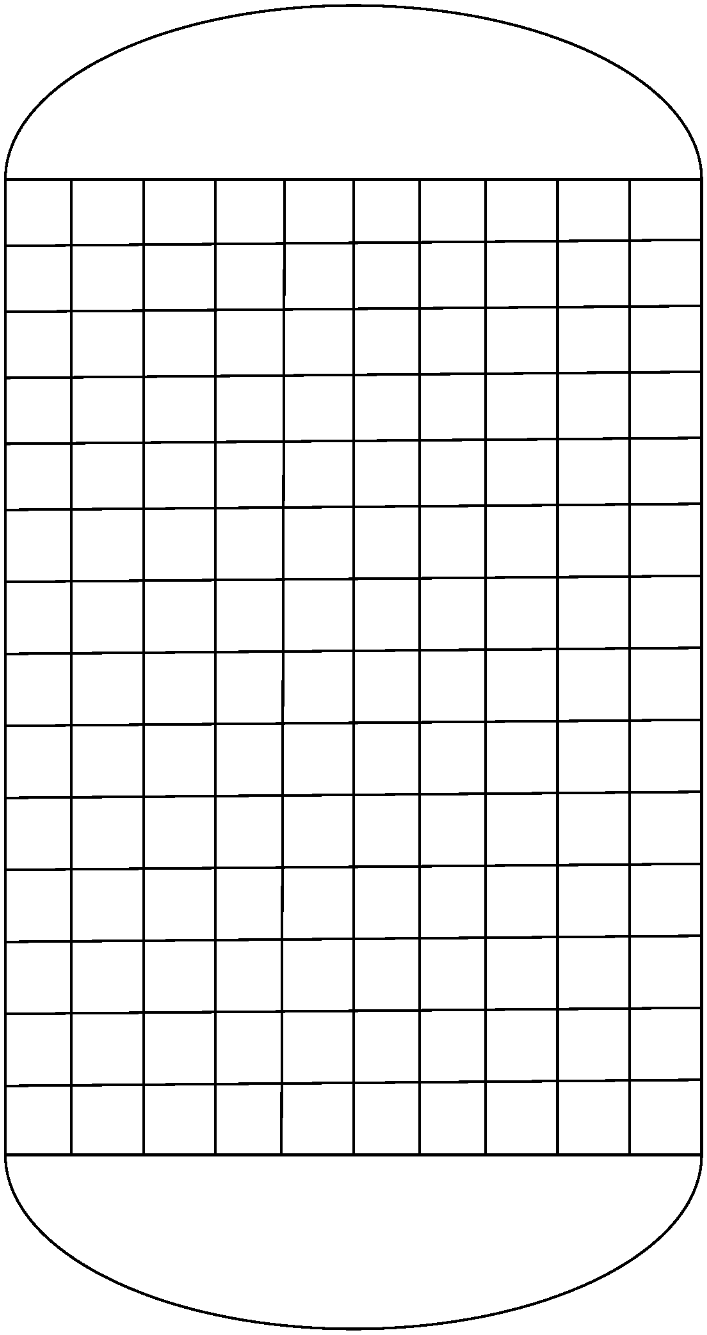
FIG. 1 shows examples of ice cube molds used for the production of standardized concrete coupons by filling 1-$cm^3$ silicone ice cube molds with ready-mix concrete.

FIG. 1 shows examples of ice cube molds used for the production of standardized concrete coupons by filling 1-$cm^3$ silicone ice cube molds with ready-mix concrete. All cubes were air dried for a minimum of three days at room temperature before removal from the silicone trays. Individual concrete coupons were rinsed in deionized water and sterilized by autoclaving at 121° C. for 15 min.

Figure 2:
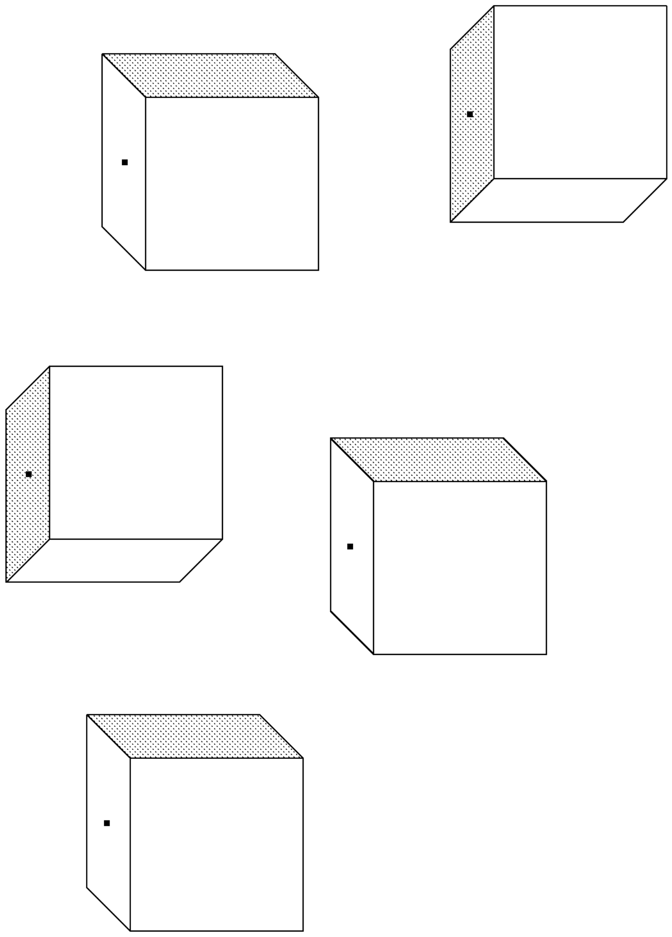
FIG. 2 shows an example of FMDV dried on concrete coupons.

FIG. 2 shows an example of FMDV dried on concrete coupons.

Concrete Carbonation

Concrete coupons that received carbonation treatment were placed in a standard $CO_2$ incubator typically used for mammalian tissue culture (Sanyo model MCO-18AIC) for 7 days. The internal temperature was held constant at 37° C., and ambient air was continuously supplemented with $CO_2$ to obtain a final concentration of 5% $CO_2$, as measured by an infrared $CO_2$ sensor. Incubator humidity was regulated by natural vaporization of water in a humidifying pan. Relative humidity (rH) values, measured using a digital rH meter (ThermoPro TP-50), remained stable at 88% throughout the 7-day incubation. Carbonated concrete coupons were sterilized by autoclaving, which did not change coupon surface pH. As part of the methods development, the researchers found that exposing concrete coupons to dry ice, sublimating $CO_2$, in a sealed container at room temperature for a period of three days, was ineffective at inducing carbonation, presumably due to the low temperature and lack of humidity.

pH Measurements

The pH of concrete matrices was measured using two methods. First, phenolphthalein is a pH indicator dye that remains colorless at pH values below 8.5, and becomes increasingly darker as pH increases above 8.5 (CID=4764, https://pubchem.ncbi.nlm.nih.gov/compound/4764.

Accessed 9 Dec. 2019). To obtain an approximate qualitative pH value of the concrete surface before and after carbonation, 50 μl of a liquid phenolphthalein solution was applied across the surface of the 1-$cm^3$ concrete cubes and the color change recorded. At pH values >8.5, the concrete coupon surface changed color from grey to magenta. Second, a quantitative pH measurement was obtained by crushing the concrete coupons to generate concrete "dust," which was mixed with deionized water and the solution measured directly with a digital pH meter. Specifically, carbonated and un-carbonated coupon cubes were placed between sheets of paper, crushed with a hydraulic press, and the output sifted through a wire mesh (⅛ inch) to obtain a uniform mixture of fine dust particles. Five grams of the concrete dust was combined with 10 ml of deionized water in a 50-ml conical tube and vortexed. After sedimentation of the dust particles by gravity, the pH of the supernatant liquid was measured with an Oakton handheld digital pH meter (Cole Parmer, EW-35423-01).

Soil Load Preparation

The standardized soil load was prepared by combining individual component stocks of 5.0% yeast extract (Cole Parmer, BP142210), 5.0% bovine serum albumin (BSA; Cole Parmer, BP6711) and 0.4% bovine mucin dissolved in sterile phosphate-buffered saline (PBS). Component stocks were prepared in 10-ml volumes, filter-sterilized through a 0.2-μm filter, divided into single-use aliquots (1 ml) and stored at −20° C. until combined into a standard soil load.

A Concrete Coupons Production Method

According to one embodiment, concrete testing coupons were produced by separating the coarse aggregate from an 80-pound bag of Sakrete High-Strength Concrete Mix and combining 438 g of the fine cementitious material with 100 mL of tap water. The wet concrete slurry was poured into easy-release silicone ice cube trays to standardize size, shape, and volume (one hundred and sixty 1-$cm^3$ cubes/tray). The cubes were air-dried for five days at room temperature before removal. Hardened coupons were carbonated to lower the surface pH by incubation in a standard laboratory $CO_2$ incubator (Sanyo model MCO-18AIC) set at 37° C. with 5% $CO_2$ and 88% relative humidity for seven days. Carbonated concrete coupons (cubes) were washed three times in deionized water and sterilized by autoclaving in an autoclave for fifteen minutes at 121° C. Surface neutrality was confirmed with the indicator phenolphthalein.

Stainless steel coupons (brushed stainless steel disks type 430, 1 cm diameter, 0.7 mm thick) were obtained from Pegen Industries Inc., Ontario, Canada. Coupons were washed and degreased for 30 minutes in a 10% (w/v) solution of Alconox detergent (prepared according to the manufacturer's instructions), rinsed three times in deionized water, and dried in a biological safety cabinet. Each coupon was visually inspected and discarded if abnormalities (i.e., rust, chipping) were observed. Coupons passing visual inspection were transferred to 150 mm glass petri dishes lined with Whatman Type 1 filter paper and sterilized by autoclaving for 45 minutes at 121° C. prior to use.

A 1-cm stainless steel magnetic disc was glued to each concrete test coupon to allow placement vertically and inverted on room surfaces. Further addition of concrete test coupon to sample boxes containing magnetic strips for hanging in multiple orientations (horizontal, vertical, and inverted orientations) will allow for testing the efficacy of fogs, vapors, gases. The coupons can be pre-inoculated and dried with any test organism of interest (i.e., bacteria, spores, viruses, fungi) in the soil load of the user's choosing.

Virucidal Efficacy Testing

1. Equipment

The Binary Ionization Technology (BIT) process activates and ionizes a solution of 7.8% Hydrogen Peroxide ($H_2O_2$) into a fine mist and fog called ionized Hydrogen Peroxide (iHP). The Tomi SteraMist® Environment System is a complete room fogging decontamination system, which is transportable, automated, and remote-controlled, and provides complete room decontamination using three (3) applicators per system. The SteraMist® Environment System was used as a complete room disinfection system. Visible fog moves like gas through the area being treated. The system has one programmable unit with 3 iHP spray ports. It is portable, automated, and remote-controlled. A complete room treatment could be performed in just over 75 minutes for a 3,663.7 $ft^3$ room, including application time, contact time, and aeration time. Less time is typically needed for smaller size rooms. The room is safe to enter once hydrogen peroxide is below 0.2 ppm.

SteraMist's iHP technology utilizes cold plasma and a low percentage hydrogen peroxide proprietary blend solution to kill on contact for a quick disinfection & decontamination of targeted areas, objects, and large full room spaces. The cold plasma arc produces electric energy breaking down hydrogen peroxide bonds into a powerful natural killing agent that disperses as a mist resulting in full coverage disinfection. The cold plasma involves the use of 7.8% hydrogen peroxide BIT Solution which converts to iHP after passing through a cold plasma arc. For the dispersion, the iHP is carried throughout the mist, moving like a gas throughout the treated area.

2. Room Setup

The room is a BSL3-Ag Vivarium (50×26×10 feet=13,000 $ft^3$). Inside the room are a taped off shower and feed room, two SteraMist® environment systems, six iHP sprayers with motorized rotating heads, and three fans set up in the room (for aeration purposes to clear the space after iHP dwell time, not used to circulate chemical during test). The HVAC is shut down during runs.

3. Sample Preparation

OECD (Organization for Economic Cooperation and Development) Test method (similar to ASTM E2197) was used for sample preparation. Viral inoculum was prepared with 3-part soil load (BSA (Bovine Serum Albumin), Yeast Extract, Bovine mucin). 10-μL virus inoculum was spotted on coupons and dried in BSC (Biological Safety Cabinet). The samples include 1-cm stainless steel disks and 1-$cm^3$ carbonated concrete pieces (cubes).

Sample boxes are prepared. Each sample box includes steel and concrete coupons for FMDV, steel and concrete coupons for ASFV, Biological Indicator (BI), six log GST spores (Mesa Labs), and Chemical Indicator (CI) strip.

4. Sample Setup

Sample boxes containing BIs, CIs, and coupons (steel and concrete) inoculated with ASFV and FMDV were transferred from lab to test room. Thirty-six (36) sample locations were in an evenly dispersed "grid" format throughout the room. Attempts were made to include "high, medium, low" sampling sites on vertical wall surfaces, in addition to the ceiling and floor. Individual boxes were attached at each location with magnetic tape.

Figure 3:
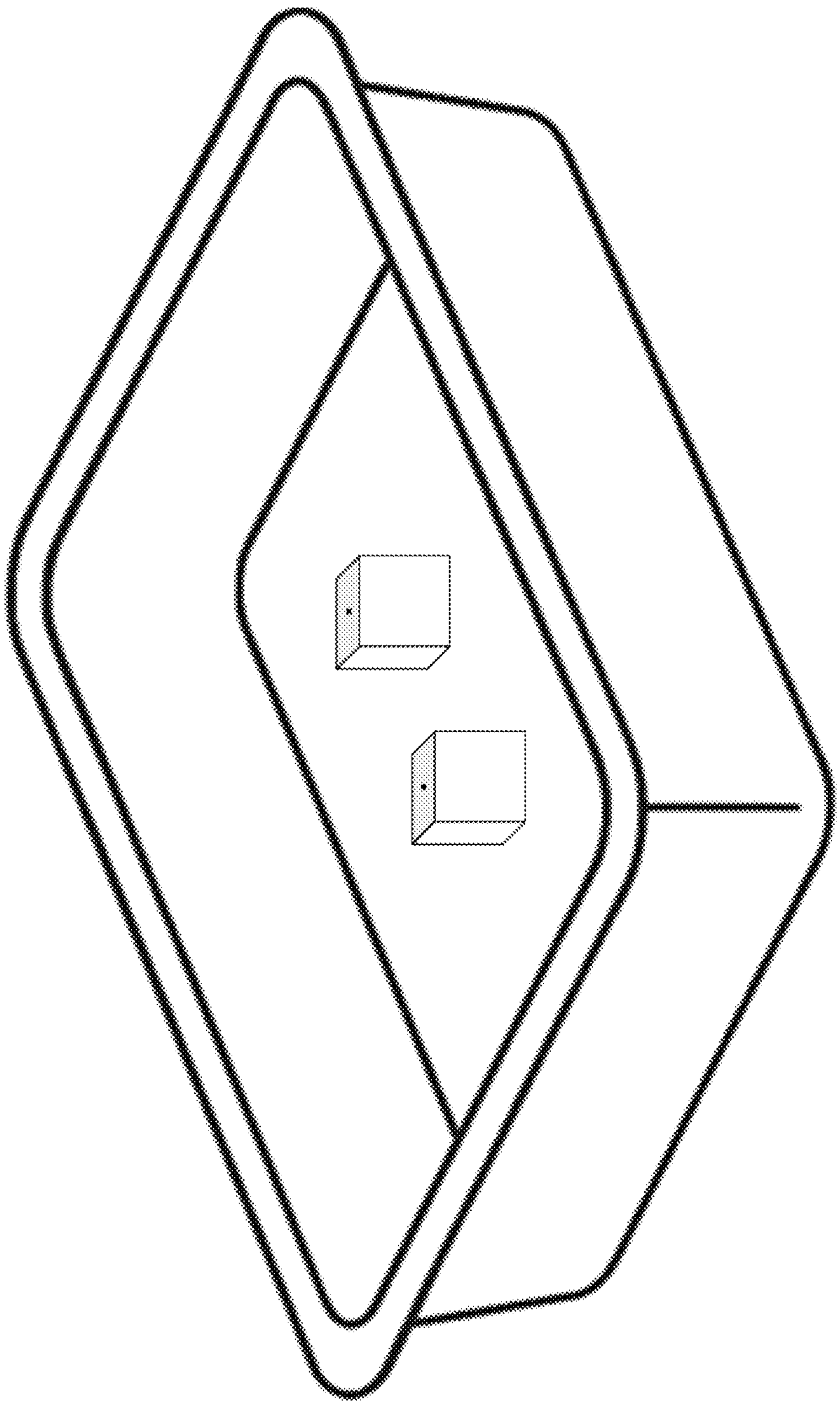
FIG. 3 shows an example of a sample setup including a container for the concrete coupons of FIG. 2.

FIG. 3 shows an example of a sample setup including a container for the concrete coupons of FIG. 2.

Figure 4:
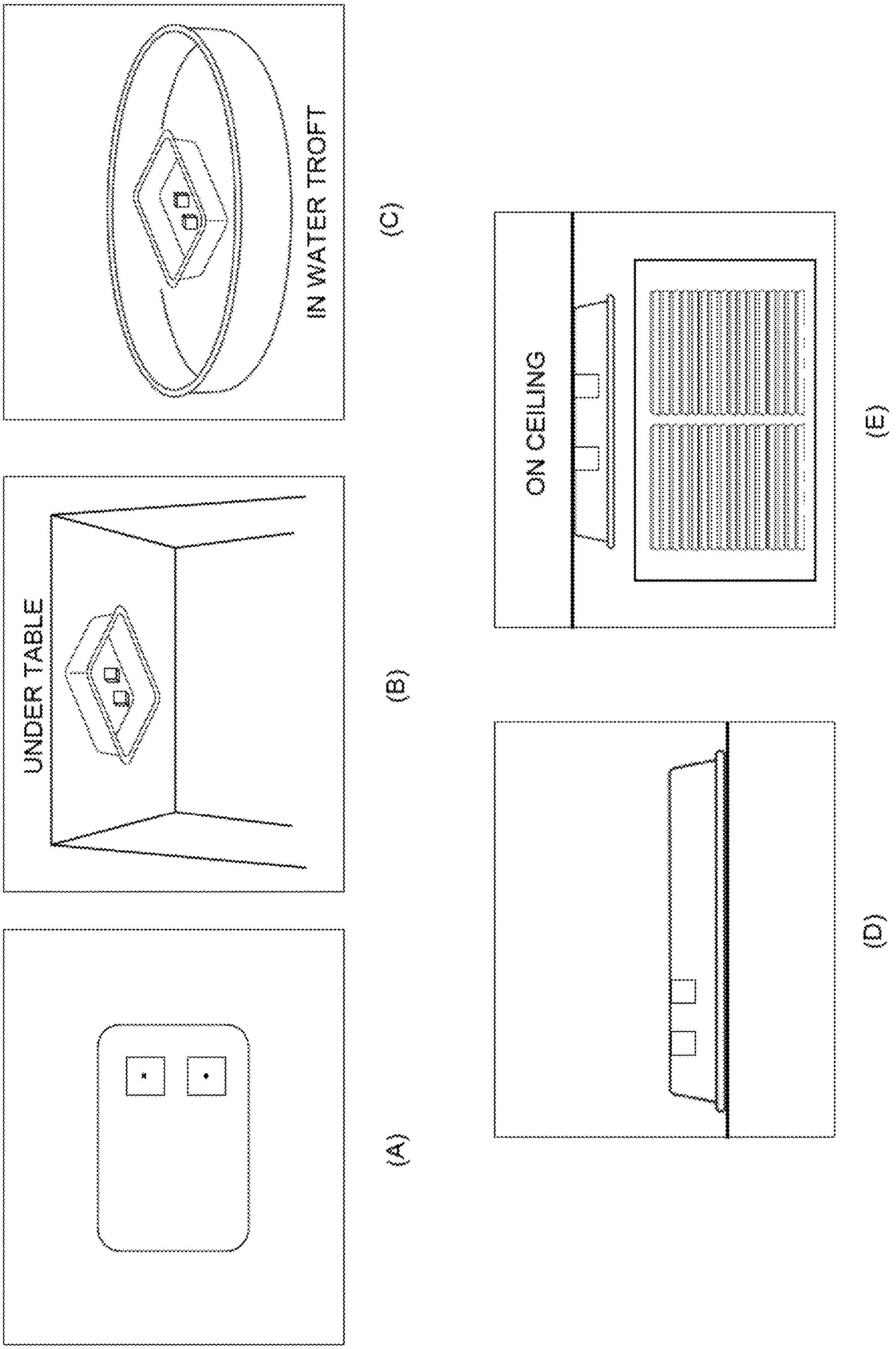
FIG. 4 shows other examples of sample setup including (A) sample disposed vertically on a wall, (B) sample inverted under a steel table, (C) sample placed in the bottom of a water troft, (D) sample placed upside down on the floor, and (E) sample on the ceiling near a ventilation duct.

FIG. 4 shows other examples of sample setup including (A) sample disposed vertically on a wall, (B) sample inverted under a steel table, (C) sample placed in the bottom of a water troft, (D) sample placed upside down on the floor, and (E) sample on the ceiling near a ventilation duct.

5. Run Conditions

FIG. 5 is a Table of run conditions. Four tests are shown. The run conditions include BIT solution concentration, iHP dose, dwell time, and aeration time.

The iHP system has no requirements for a room to be pre-conditioned to certain temperature/humidity. The injection/dwell time is dependent on the room size.

6. Sample Recovery and Analysis

Figure 6:
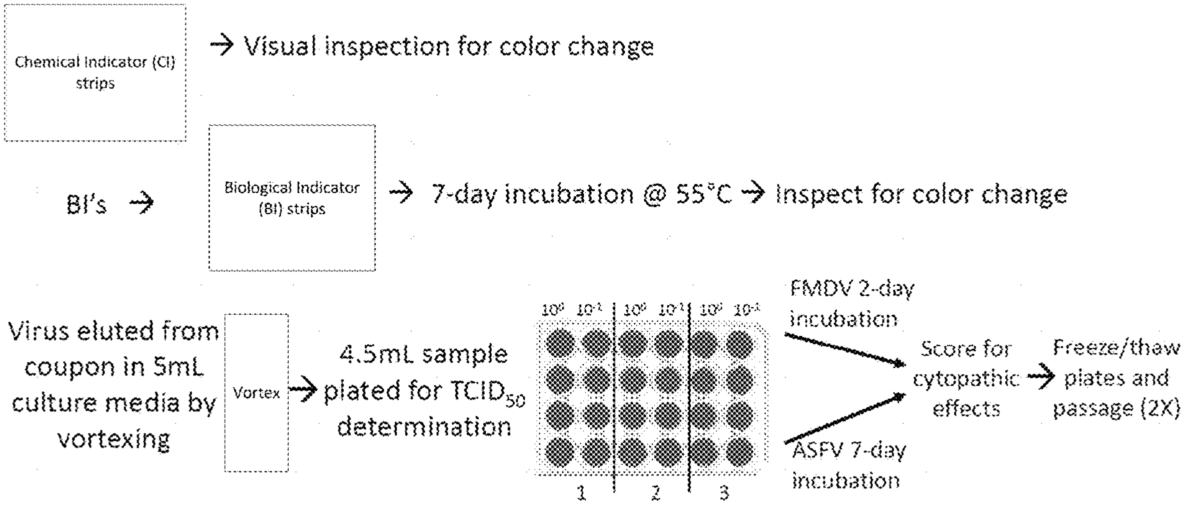
FIG. 6 is a flow diagram illustrating an example of sample recovery and analysis.

FIG. 6 is a flow diagram illustrating an example of sample recovery and analysis. The CI (Chemical Indicator) strips are visually inspected for color change. The BI (Biological Indicator) strips are incubated for 7 days at 55° C. in appropriate media and visually inspected for spore growth. The virus is eluted from each coupon in 5 mL culture media by vortexing. A 4.5 mL sample is plated for $TCID_{50}$ determination. The samples are incubated at 37° C. for either 2 days (FMDV) or 7 days (ASFV). Thereafter, the sample are scored for cytopathic effects. A subsequent step is performed to freeze/thaw the plates and passage (2X).

7. Tests and Test Results on Virucidal Efficacy

Test #1 and Test #2 were conducted to obtain virucidal efficacy results in duplicate tests using the Binary Ionization Technology® (BIT™) Solution at a nominal concentration of 7.6% and the lower certified limit (LCL) of 7.4% to replicate a "worst case scenario." The tests use both viruses (FMDV and ASFV) dried on non-porous (stainless steel) and porous (concrete) surface types. They employ a 15-minute dwell time.

All BIs from all four tests (n-144) were negative for spore growth. All CIs from all four tests (n=144) were positive for $H_2O_2$ exposure.

Figure 7:
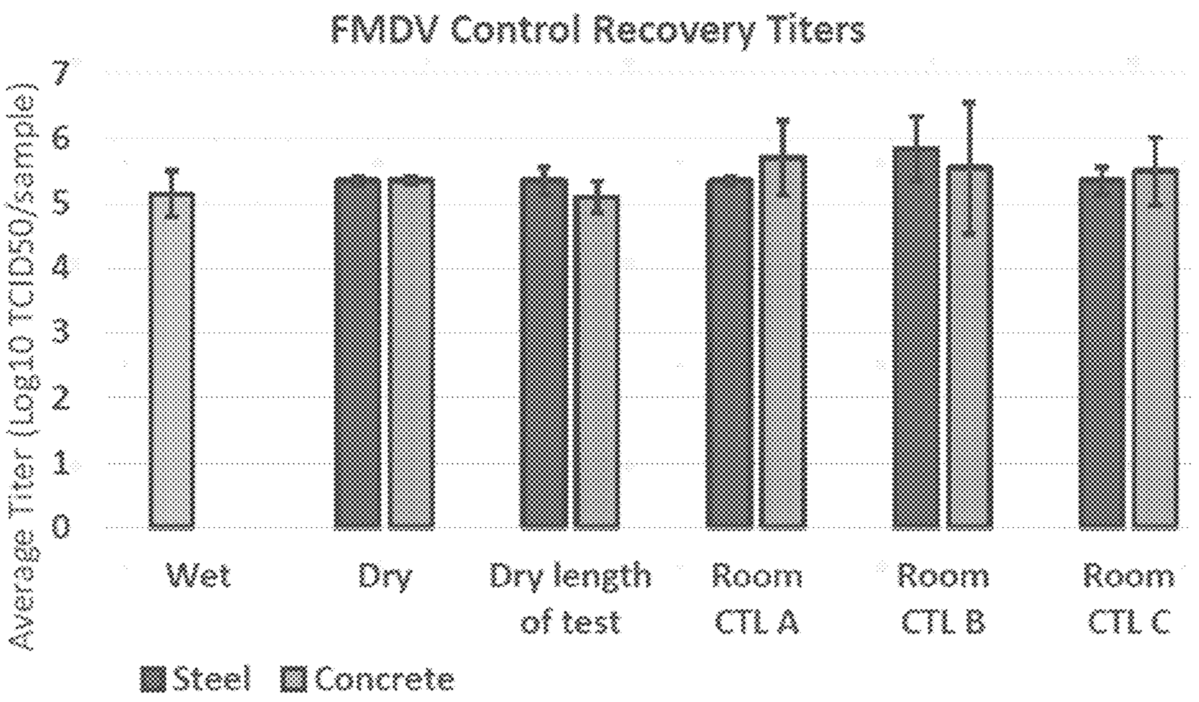
FIG. 7 is a graphical diagram of the average FMDV control recovery titers for Test #1 and Test #2.

FIG. 7 is a graphical diagram of the average FMDV control recovery titers for Test #1 and Test #2.

Figure 8:
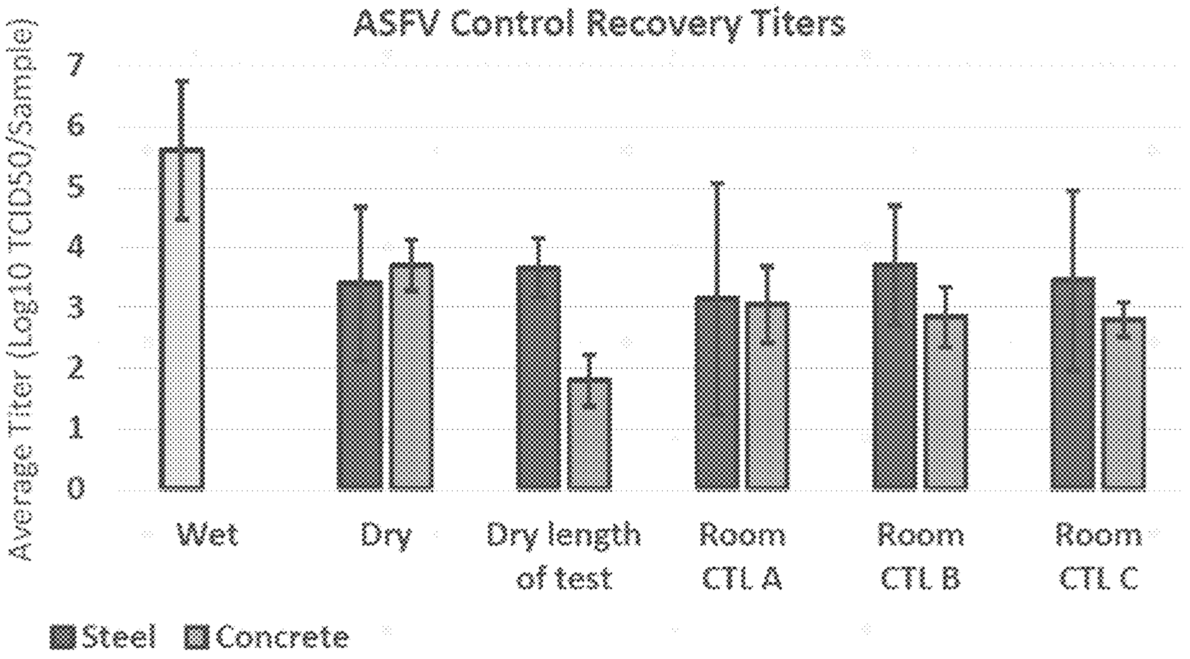
FIG. 8 is a graphical diagram of the average ASFV control recovery titers for Test #1 and Test #2.

FIG. 8 is a graphical diagram of the average ASFV control recovery titers for Test #1 and Test #2.

FIG. 9 is a Table of ASFV and FMDV results for Test #1 with 7.6% hydrogen peroxide.

FIG. 10 is a Table of ASFV and FMDV results for Test #2 with 7.4% hydrogen peroxide.

The results show effective room coverage/dispersion due to positivity of all CIs and 100% negativity of all BI's.

For Test #1 and Test #2 on ASFV, there was a complete kill on stainless steel and concrete with both 7.6% and 7.4% iHP.

For Test #1 and Test #2 on FMDV, there was a complete kill on stainless steel with both 7.6% and 7.4% iHP. The iHP (at either concentration) was not able to completely inactivate FMDV dried on concrete.

8. Test and Test Results on FMDV Kill

Test #3 and Test #4 were conducted to determine if complete FMDV kill is achievable using extended dwell/contact times for $H_2O_2$ fog. The tests use only FMDV dried on concrete. They involve testing with 60-minute and overnight (~16 hours) contact time at LCL (7.4% $H_2O_2$).

FIG. 11 is a Table of FMDV results for Test #3 with 7.4% hydrogen peroxide.

FIG. 12 is a Table of FMDV results for Test #4 with 7.4% hydrogen peroxide.

The tests involve testing product at LCL on concrete against FMDV, at 15-minute dwell: 21/36 positive, 60 minute dwell: 6/36 positive, and 16 hour dwell: 0/36 positive.

Longer dwell time was successful for complete FMDV inactivation.

FIG. 13 is a Table of test results of location versus positivity.

No relationship was detected between specific sampling location and instance of positivity. No relationship was detected between general location (i.e., ceiling) and positivity.

The iHP™ appears to be a promising technology for decontamination/fumigation/inactivation of FMDV and ASFV on non-porous laboratory surfaces. Porous surfaces such as concrete may require extended dwell times for difficult-to-kill organisms such as small non-enveloped viruses.

Both ASFV and FMDV were inactivated by iHP on non-porous stainless steel a dwell time of 15 minutes at both nominal (7.6%) and lower certified product concentration limit (7.4%). ASFV was inactivated on porous concrete with a dwell time of 15 minutes at both the nominal (7.6%) and lower certified product concentration limit (7.4%). Complete inactivation of FMDV on concrete required a dwell time of 16 hours (overnight) when testing at 7.4% $H_2O_2$.

Passaging of virus samples 3× in tissue culture increased the overall sample positivity and is useful for detecting low levels of infectious virus.

Methodology

Figure 14:
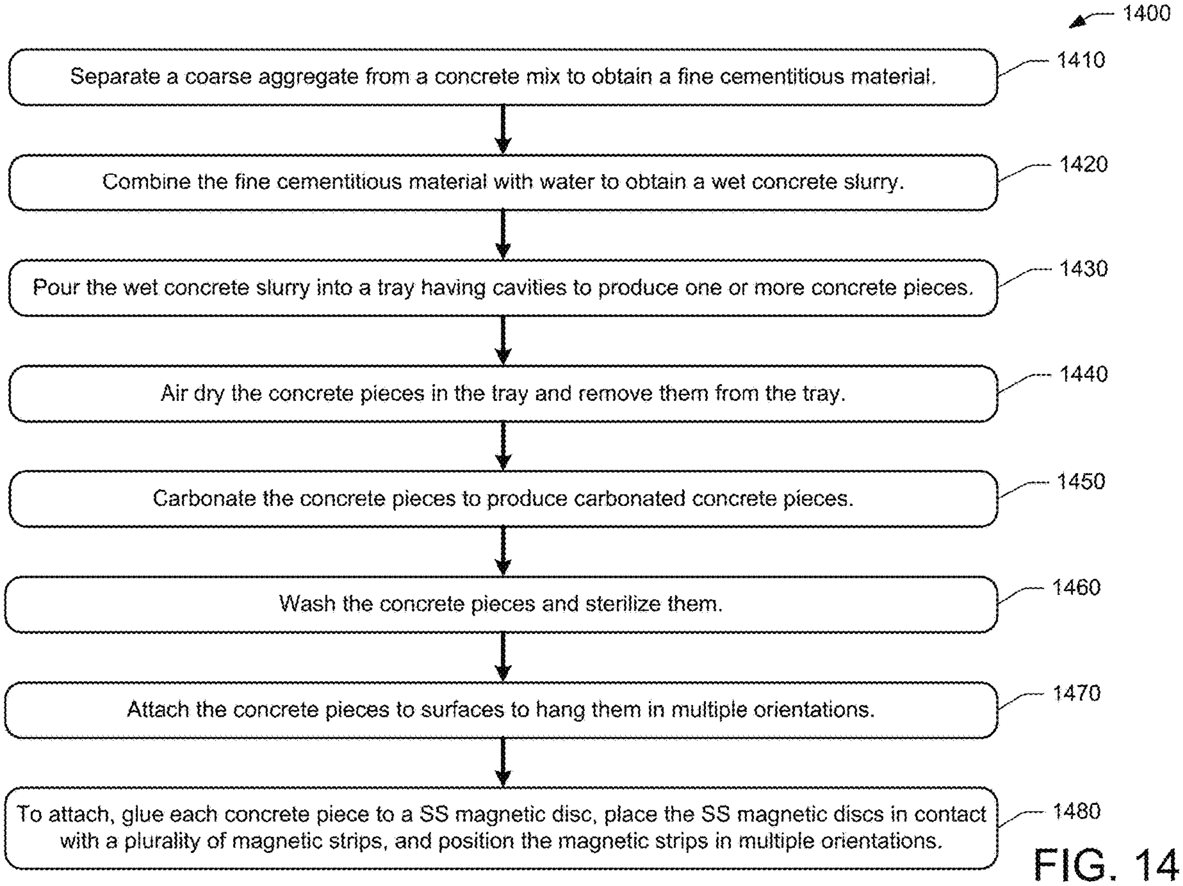
FIG. 14 is a flow diagram illustrating an example of a method of producing concrete test pieces or coupons for monitoring decontamination processes and efficacy.

FIG. 14 is a flow diagram illustrating an example of a method of producing concrete test pieces or coupons for monitoring decontamination processes and efficacy 1400.

Step 1410 involves separating a coarse aggregate from a concrete mix to obtain a fine cementitious material. Step 1420 combines the fine cementitious material with water to obtain a wet concrete slurry. In step 1430, the wet concrete slurry is poured into a tray having cavities to produce one or more concrete pieces or coupons. The tray may be a cube tray having one or more cube cavities to receive the wet concrete slurry to produce one or more concrete cubes. Step 1440 involves air drying the concrete pieces in the tray and removing them from the tray. Step 1450 carbonates the concrete pieces to produce carbonated concrete pieces. In step 1460, the concrete pieces are washed and sterilized. In step 1470, the concrete pieces are attached to surfaces to hang them in multiple orientations (e.g., horizontal orientation, vertical orientation, inverted orientation, etc.) for monitoring decontamination processes and efficacy. Attaching the concrete pieces may include gluing each concrete piece to a stainless steel (SS) magnetic disc, placing the SS magnetic discs in contact (magnetic contact) with a plurality of magnetic strips, and positioning the magnetic strips in multiple orientations (step 1480).

The inventive concepts taught by way of the examples discussed above are amenable to modification, rearrangement, and embodiment in several ways. Accordingly, although the present disclosure has been described with reference to specific embodiments and examples, persons skilled in the art will recognize that changes may be made in form and detail without departing from the spirit and scope of the disclosure.

An interpretation under 35 U.S.C. § 112(f) is desired only where this description and/or the claims use specific terminology historically recognized to invoke the benefit of interpretation, such as "means," and the structure corresponding to a recited function, to include the equivalents thereof, as permitted to the fullest extent of the law and this written description, may include the disclosure, the accompanying claims, and the drawings, as they would be understood by one of skill in the art.

To the extent the subject matter has been described in language specific to structural features and/or methodological steps, it is to be understood that the subject matter defined in the appended claims is not necessarily limited to the specific features or steps described. Rather, the specific features and steps are disclosed as example forms of implementing the claimed subject matter. To the extent headings are used, they are provided for the convenience of the reader and are not to be taken as limiting or restricting the systems, techniques, approaches, methods, devices to those appearing in any section. Rather, the teachings and disclosures herein can be combined, rearranged, with other portions of this disclosure and the knowledge of one of ordinary skill in the art. It is the intention of this disclosure to encompass and include such variation.

The indication of any elements or steps as "optional" does not indicate that all other or any other elements or steps are mandatory. The claims define the invention and form part of the specification. Limitations from the written description are not to be read into the claims.

What is claimed is:

1. A sample setup comprising a plurality of concrete test coupons, each concrete test coupon including a sterilized, carbonated, dried concrete piece formed from a wet concrete slurry including a combination of water and a fine cementitious material which is obtained by separating a coarse aggregate from a concrete mix, wherein each test coupon has a surface pH of less than 8.5;

the plurality of concrete test coupons being attached to a plurality of surfaces of different orientations to hang the concrete test coupons arranged in multiple orientations in a room, wherein the test coupons reside within one or more sample boxes each comprising a closeable lid; and the multiple orientations including a ceiling ventilation orientation by being attached on a ceiling of the room at a location spaced from and near a ventilation duct, a bottom orientation by being placed on a bottom of a water trough in the room, an inverted orientation by being attached inverted under a table in the room, an upside down orientation by being placed upside down on a floor of the room, and a vertical orientation by being attached vertically to a wall of the room.

2. The sample setup of claim 1, further comprising:

a plurality of stainless steel magnetic discs, each concrete test coupon being glued to a stainless steel magnetic disc of the plurality of stainless steel magnetic discs; and a plurality of magnetic strips positioned in the multiple orientations by being attached to the plurality of surfaces of different orientations;

wherein the stainless steel magnetic discs are placed in contact with the plurality of magnetic strips, each magnetic strip having a longitudinal dimension along a longitudinal direction, each magnetic strip including multiple stainless steel magnetic discs of the plurality of stainless steel magnetic discs arranged along the longitudinal direction.

3. The sample setup of claim 1, wherein each concrete test coupon is a concrete cube.

4. The sample setup of claim 3, wherein the concrete cube has a volume of about 1 $cm^3$.

5. The sample setup of claim 1, wherein each concrete piece is air dried for five days at room temperature to form a dried concrete piece before being carbonated.

6. The sample setup of claim 5, wherein the dried concrete piece is carbonated by incubation in a $CO_2$ incubator at 37° C. with 5% $CO_2$ and 88% relative humidity for seven days to form a carbonated, dried concrete piece.

7. The sample setup of claim 6, wherein the carbonated concrete piece is washed three times in deionized water and sterilized in an autoclave for 15 minutes at 121° C. to form the sterilized, carbonated, dried concrete piece.

8. A sample setup comprising a plurality of concrete test coupons, each concrete test coupon including a sterilized, carbonated, dried concrete piece formed from a wet concrete slurry including a combination of water and a fine cementitious material which is obtained by separating a coarse aggregate from a concrete mix, wherein each test coupon has a surface pH of less than 8.5;

the plurality of concrete test coupons including groups of concrete test coupons, each group being arranged in a different orientation of a plurality of orientations in a room, wherein the test coupons reside within one or more sample boxes each comprising a closeable lid; and the plurality of orientations including a ceiling orientation by being attached on a ceiling of the room at a location spaced from and near a ventilation duct, a floor orientation by being placed on a floor of the room, a wall orientation by being attached to wall surfaces of the room at different heights, a bottom orientation by being placed on a bottom of a water trough in the room, an inverted orientation by being attached inverted under a table in the room, and an upside down orientation by being placed upside down on the floor of the room.

9. The sample setup of claim 8, wherein the plurality of concrete test coupons include concrete test coupons which are positioned in the ceiling orientation, the floor orientation, and the wall orientation in an evenly dispersed grid format throughout the room.

10. The sample setup of claim 8, wherein 36 concrete test coupons are positioned in the ceiling orientation, the floor orientation, and the wall orientation in an evenly dispersed grid format throughout the room.

11. The sample setup of claim 8, further comprising:

a plurality of stainless steel magnetic discs, each concrete test coupon being attached to a stainless steel magnetic disc of the plurality of stainless steel magnetic discs, the groups of concrete test coupons attached to corresponding groups of the stainless steel magnetic discs; and a plurality of magnetic strips, each magnetic strip having a longitudinal dimension along a longitudinal direction, each group of the groups of stainless steel magnetic discs being attached to a corresponding one magnetic strip along the longitudinal direction of the plurality of magnetic strips;

wherein the magnetic strips are positioned to arrange the groups of concrete test coupons attached to the corresponding groups of stainless steel magnetic discs in the plurality of different orientations.

12. The sample setup of claim 8, wherein each concrete test coupon is a concrete cube having a volume of about 1 $cm^3$.

13. The sample setup of claim 8, wherein each concrete piece is air dried for five days at room temperature to form a dried concrete piece before being carbonated.

14. The sample setup of claim 13, wherein the dried concrete piece is carbonated by incubation in a $CO_2$ incubator at 37° C. with 5% $CO_2$ and 88% relative humidity for seven days to form a carbonated, dried concrete piece.

15. The sample setup of claim 14, wherein the carbonated concrete piece is washed three times in deionized water and sterilized in an autoclave for 15 minutes at 121° C. to form the sterilized, carbonated, dried concrete piece.

16. A sample setup comprising:

a plurality of concrete test coupons;

each concrete test coupon including a sterilized, carbonated, dried concrete piece formed from a wet concrete slurry including a combination of water and a fine cementitious material which is obtained by separating a coarse aggregate from a concrete mix, wherein each test coupon has a surface pH of less than 8.5; and the plurality of concrete test coupons including groups of concrete test coupons which are arranged in a plurality of different orientations in a room;

a plurality of stainless steel magnetic discs, each concrete test coupon being attached to a stainless steel magnetic disc of the plurality of stainless steel magnetic discs, the groups of concrete test coupons attached to corresponding groups of the stainless steel magnetic discs; and a plurality of magnetic strips, each magnetic strip having a longitudinal dimension along a longitudinal direction, each group of the groups of stainless steel magnetic discs being attached to a corresponding one magnetic strip along the longitudinal direction of the plurality of magnetic strips;

the magnetic strips being positioned to arrange the groups of concrete test coupons attached to the corresponding groups of stainless steel magnetic discs in the plurality of different orientations; and the plurality of different orientations including a ceiling orientation by being attached on a ceiling of the room at a location spaced from and near a ventilation duct, a floor orientation by being placed on a floor of the room, a wall orientation by being attached to wall surfaces of the room at different heights, a bottom orientation by being placed on a bottom of a water trough in the room, an inverted orientation by being attached inverted under a table in the room, and an upside down orientation by being placed upside down on the floor of the room.

17. The sample setup of claim 16, wherein each concrete test coupon is a concrete cube having a volume of about 1 $cm^3$.

18. The sample setup of claim 16, wherein each concrete piece is air dried for five days at room temperature to form a dried concrete piece before being carbonated.

19. The sample setup of claim 18, wherein the dried concrete piece is carbonated by incubation in a $CO_2$ incubator at 37° C. with 5% $CO_2$ and 88% relative humidity for seven days to form a carbonated, dried concrete piece.

20. The sample setup of claim 19, wherein the carbonated concrete piece is washed three times in deionized water and sterilized in an autoclave for 15 minutes at 121° C. to form the sterilized, carbonated, dried concrete piece.

* * * * *